US012618047B2

(12) United States Patent
Morizur et al.

(10) Patent No.: US 12,618,047 B2
(45) Date of Patent: May 5, 2026

(54) AUTOMATED METHOD FOR PREPARING KERATINOCYTES

(71) Applicants:Centre D'Etude Des Cellules Souches (CECS), Corbeil-Essonnes (FR); Universite Evry Val D'Essonne, Evry-Courcouronnes (FR)

(72) Inventors: Lise Morizur, Pontault-Combault (FR); Léa Lesueur, Villabe (FR); Christine Baldeschi, Villemoisson sur Orge (FR)

(73) Assignees: Centre d'Etude des Cellules Souches, Essonnes (FR); Universite Evry Val D'Essonne, Evry-Courcouronnes (FR)

( * ) Notice: Subject to any disclaimer, the term of this patent is extended or adjusted under 35 U.S.C. 154(b) by 824 days.

(21) Appl. No.: 17/909,354

(22) PCT Filed: Mar. 2, 2021

(86) PCT No.: PCT/EP2021/055192
§ 371 (c)(1),
(2) Date: Sep. 2, 2022

(87) PCT Pub. No.: WO2021/175860
PCT Pub. Date: Sep. 10, 2021

(65) Prior Publication Data
US 2023/0113241 A1     Apr. 13, 2023

(30) Foreign Application Priority Data
Mar. 2, 2020     (EP) ..................................... 20305218

(51) Int. Cl.
*C12N 5/071*          (2010.01)
(52) U.S. Cl.
CPC ...... *C12N 5/0629* (2013.01); *C12N 2501/155* (2013.01); *C12N 2501/385* (2013.01); *C12N 2506/45* (2013.01); *C12N 2533/50* (2013.01)
(58) Field of Classification Search
None
See application file for complete search history.

(56) References Cited

U.S. PATENT DOCUMENTS

2011/0165130 A1*  7/2011  Guenou .................. A61P 17/02
435/366

FOREIGN PATENT DOCUMENTS

| WO | 2016039687 A1 | 3/2016 |
| WO | 2016209166 A1 | 12/2016 |
| WO | 2017091547 A1 | 6/2017 |

OTHER PUBLICATIONS

Kalyanaraman, B., & Boyce, S. (2007). Assessment of an automated bioreactor to propagate and harvest keratinocytes for fabrication of engineered skin substitutes. Tissue engineering, 13(5), 983-993. (Year: 2007).*

Liu Z, Wen J, Leng X, Zhou Q, Zhou C, Zhao H, Wu X. A Simplified and Efficient Method to Isolate Primary Human Keratinocytes from Adult Skin Tissue. J Vis Exp.(138):57784. doi: 10.3791/57784. PMID: 30199027; PMCID: PMC6231857. (Year: 2018).*

Igor Kogut et al, "Differentiation of Human Induced Pluripotent Stem Cells into a Keratinocyte Lineage", "Antibody-drug conjugates; In: Methods in Molecular Biology; ISSN 1064-3745; vol. 1045", p. 1-12, Jan. 1, 2013 (Jan. 1, 2013), USHumana Press.

Sophie Domingues et al, "Differentiation of nonhuman primate pluripotent stem cells into functional keratinocytes", Stem Cell Research & Therapy, vol. 8, No. 1, Dec. 1, 2017 (Dec. 1, 2017).

Karl Gledhill et al, "Melanin Transfer in Human 3D Skin Equivalents Generated Exclusively from Induced Pluripotent Stem Cells", PLOS One, vol. 10, No. 8, Aug. 26, 2015 (Aug. 26, 2015), p. e0136713.

Metallo Christian M et al, "Directed differentiation of human embryonic stem cells to epidermal progenitors", Antibody-Drug Conjugates; In: Methods in Molecular Biology; ISSN 1064-3745; vol. 1045; [Methods in Molecular Biology; ISSN 1064-3745; vol. 1045], Humana Press, US, vol. 585, Jan. 1, 2010 (Jan. 1, 2010).

Ganna Bilousova et al, "Differentiation of Mouse Induced Pluripotent Stem Cells into a Multipotent Keratinocyte Lineage", Journal of Investigative Dermatology, vol. 131, No. 4, Apr. 1, 2011 (Apr. 1, 2011), p. 857-864.

Aneta Sciezynska et al, "Isolation and culture of human primary keratinocytes—a methods review", Experimental Dermatology, vol. 28, Jan. 1, 2019 (Jan. 1, 2019), p. 107-112.

Thomas R J et al, "Cell Culture Automation and Quality Engineering: A Necessary Partnership to Develop Optimized Manufacturing Processes for Cell-Based Therapies", Jun. 1, 2008 (Jun. 1, 2008), vol. 13, No. 3, p. 152-158.

International Search Report in connection to PCT/EP2021/055192 issued on Apr. 28, 2021.

Aasen, et al., "Isolation and cultivation of human keratinocytes from skin or plucked hair for the generation of induced pluripotent stem cells", Nature Protocols, vol. 5, No. 2, Jan. 2010, 371-381.

Chowdhury, et al., "Effect of supplementation of dermal fibroblasts conditioned medium on expansion of keratinocytes through enhancing attachment", Indian Journal of Experimental Biology, vol. 50, May 2012, pp. 332-339.

* cited by examiner

*Primary Examiner* — Anna Skibinsky
*Assistant Examiner* — Catherine L McCormick
(74) *Attorney, Agent, or Firm* — HSML P.C.

(57) ABSTRACT

The present invention relates to ex vivo methods for obtaining populations of human keratinocytes derived from human pluripotent stem cells (hPSCs).
More particularly, the present invention relates to an automated method that combines in a sequential manner automated differentiation and amplification of a population of hPSC-derived keratinocytes.

12 Claims, 2 Drawing Sheets

A.

B.

AUTOMATED METHOD FOR PREPARING KERATINOCYTES

FIELD OF THE INVENTION

The present invention relates to ex vivo methods for obtaining populations of human keratinocytes derived from human pluripotent stem cells (hPSCs).

More particularly, the present invention relates to an automated method that combines in a sequential manner automated differentiation and amplification of a population of hPSC-derived keratinocytes.

BACKGROUND OF THE INVENTION

The skin consists of self-renewing layers organized into functional units of differentiating cells with their origin in a single basal stratum of proliferating keratinocytes. The dead and dying cells that comprise the stratum corneum are continually shed during desquamation and replaced by cells derived from epidermal stem cells found in the stratum germinativum. Loss of epidermal function leads to loss of thermal regulation, reduced microbial defences, risks of desiccation, inhibited wound repair, and cosmetic concerns. In the absence of sufficient autologous donor for skin grafts, coverage of wounds with cultured human keratinocytes represents a promising option for treatment.

Furthermore, in vitro and in vivo models for human skin may represent tremendous tools for studying the lineage of epidermis cells or for testing cosmetic and pharmaceutical compounds for therapeutic or toxicological effects. For example the need for in vitro models is strengthened by the fact that there is an incentive to provide an alternative to the use of animals for testing compounds and formulations.

In addition, a number of diseases affect the function of keratinocytes, either cell autonomously or through alteration of their ability to form the pluristratified epidermal tissue. In vitro and in vivo models for human skin may represent ways to reveal molecular mechanisms of diseases and, as a consequence, identify pharmacological or biological compounds endowed with therapeutic potentials.

Thus, there is a need for methods for obtaining populations of human keratinocytes that may then be useful for skin therapy or for obtaining in vitro and in vivo models for human skin. Embryonic stem cells and somatic cells that are genetically reprogrammed in order to replicate all characteristics of embryonic stem cells (such as, for example, those called "iPS" cells, for "induced pluripotent stem" cells) are pluripotent stem cells with an extensive proliferative capacity and accordingly offer a great potential use in research and medicine. Several attempts have therefore been described in the prior art for obtaining human keratinocytes from pluripotent stem cells.

To date, several groups have reported procedures to differentiate human ES/iPS cells into epidermal keratinocytes.

For example, US2009075374 describes a method of generating p63-positive cells, comprising the step of culturing embryoid bodies (EBs) in a medium comprising a retinoid and a bone morphogenetic protein for about two days to about nine days.

WO2016061071 describes a method for providing engraftable keratinocyte stem cells by differentiation of pluripotent stem cells comprising (a) forming aggregates of the pluripotent stem cells in a suspension culture in the presence of a defined basal medium; (b) culturing the aggregates in a suspension culture in the presence of an initiation culture medium comprising retinoic acid and BMP4 to effect the formation of initiated aggregates; (c) culturing the initiated aggregates in a keratinocyte progenitor culture medium comprising cholera toxin and a TGFβR1 kinase inhibitor to effect the formation of a cell population comprising keratinocyte progenitors; and (d) culturing the keratinocyte progenitors in a keratinocyte stem cell maturation medium to effect the formation of a cell population comprising engraftable keratinocyte stem cells.

WO2009156398 describes a method for obtaining a population of human keratinocytes derived from human pluripotent stem cells comprising a step of co-culturing human pluripotent stem cells with a layer of feeder fibroblasts in the presence of a keratinocyte culture medium supplemented with BMP-4 and ascorbic acid. The keratinocyte culture medium is further supplemented with one or more agents selected from the group consisting of glutamine, epidermal growth factor (EGF), sodium pyruvate, adenine, insulin, hydrocortisone, choleric toxin and triodothyronin. The keratinocytes obtained from the pluripotent stem cells co-express the keratinocyte markers keratin 5 (K5) and keratin 14 (K14). However, the flow cytometry analysis of the expression of K5 and K14 in keratinocytes shows the presence of two types of keratinocytes.

Although the differentiation of hPSCs into keratinocytes became more efficient during the last years, it still remains a long and laborious process requiring meticulous manipulations from hPSCs thawing to hPSC-keratinocytes banking. Many cell culture parameters, such as seeding homogeneity, the time spent by the cells out of the incubator or the method used to isolate clumps, could impact on the proliferation and the differentiation of hPSCs. Thus, manual processing implies operator to operator variability and the quality of hPSCs and the efficiency of their differentiation into keratinocytes are currently highly dependent on technical skills. In this regard, automation should not only allow scaling up the production of hPSC-keratinocytes but should also increase its robustness. It also could enable larger and more reliable cell production for clinical and disease modeling applications.

Until recently, the requirement of a manual enrichment to obtain a pure population of hPSC-keratinocytes prevented the use of these automated systems for the differentiation of this cell type.

Thus, a need exists for developing a fully automated process allowing a large-scale production of hPSC-keratinocytes.

Considering that, in addition to considerably complicate the process, the use of numerous growth factors and small molecules on a large scale is very expensive, especially for an automated process which requires significant dead volumes, the Applicant answers this need by providing a simplified keratinocytes differentiation protocol amenable for automation.

SUMMARY OF THE INVENTION

In accordance with a first embodiment, the present invention provides the use of a protocol amenable for an automated method that combines in a sequential manner automated differentiation and amplification of a population of hPSC-derived keratinocytes. This novel differentiation protocol associated with the use of cell culture robots open new possibilities for the production of large batches of hPSC-keratinocytes while maintaining a high cell purity and functionality.

Thus, an object of the present invention is to provide methods for large-scale automated production of keratinocytes derived from (human) pluripotent stem cells.

The hPSCs in the culture system of the methods disclosed herein are differentiating hPSCs, i.e. a population of hPSCs initially in an undifferentiated state, then induced to undergo initial stages of differentiation, the majority of said cells have been induced to undergo initial stages of differentiation. In accordance with one embodiment, the initial stage of differentiation is achieved by exposing the cells to an agent that stimulates epidermal induction and an agent that stimulates terminal differentiation of keratinocytes. In particular, the differentiating hPSCs are cultivated on a cell culture surface coated with a substrat for cell adhesion in the presence of a keratinocyte culture medium supplemented with BMP-4 and retinoic acid.

According to the present invention, the cells are not cultured in the presence of feeder cell layer.

The present invention also relates to an isolated substantially pure homogenous population of human keratinocytes derived from human pluripotent stem cells obtainable by the method as herein described.

DETAILED DESCRIPTION OF THE INVENTION

In the following description and claims use will be made, with a variety of terms, and the meaning of such terms as they should be construed in accordance with the present teaching is as follows:

As used herein, the term "epithelial marker" or "keratinocyte (KER) marker", refers to any phenotypic feature of a cell that can be used to characterize it or discriminate it from other cell types. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Specific, non-limiting examples of methods that can be used for the detection of a cell surface marker are immunohistochemistry, flow cytometry, and enzymatic analysis. Associated with each marker is the gene that encodes the transcript, and the events that lead to marker expression. A marker is said to be preferentially expressed in an undifferentiated or differentiated cell population, if it is expressed at a level that is at least 50% higher (in terms of total gene product measured in an antibody or PCR assay) or 30% more frequently (in terms of positive cells in the population) than an acceptable control.

The term "population of human keratinocytes" refers to a population of cells that is able to reconstruct a human epidermis and that is characterized by the capacity to produce keratins in the process of differentiating into the dead and fully keratinized cells of the stratum corneum. Markers of basal keratinocytes include markers of basal layer with keratin 5, 14 (K5/K14) and transcription factor ΔNp63, markers of supra basal layer with keratin 1 and keratin 10 (K1/K10), involucrin and fillagrin.

In a particular embodiment, the agent that stimulates epidermal induction is selected from the group consisting of Bone Morphogenetic Proteins (such as BMP-2, BMP-4 and BMP-7), receptor-regulated Smad proteins (such as Smad 1, Smad 5 and Smad 9) and ligands of the TGF-beta family (such as Growth and Differenciation Factor 6 GFD-6). In a preferred embodiment the agent that stimulates epidermal induction is selected from the group consisting of BMP-2, BMP-4, BMP-7, Smadi, Smad5, Smad7 and GFD-6. In a more preferred embodiment, the agent that stimulates epidermal induction is BMP-4.

As used herein, the term "organotypic culture" refers to a three-dimensional tissue culture where cultured cells are used to reconstruct a tissue or organ in vitro.

The term "cell plating" can also extend to the term "cell passaging." Cells of the invention can be passaged using cell culture techniques well known to those skilled in the art. For example, this term refers to a technique that involves the steps of (1) releasing cells from a solid support or substrate and dissociation of these cells, and (2) diluting the cells in media suitable for further cell proliferation. Cell passaging may also refer to removing a portion of liquid medium containing cultured cells and adding liquid medium to the original culture vessel to dilute the cells and allow further cell proliferation. In addition, cells may also be added to a new culture vessel that has been supplemented with medium suitable for further cell proliferation.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support.

"Undifferentiated", as used herein, refers to cultured cells when a substantial proportion (at least 80%, and possibly over 90% or 95%) of the cells and their derivatives in the population display characteristic markers and morphological characteristics of undifferentiated cells, distinguishing them from differentiated cells of embryo or adult origin. Cells are recognized as proliferating in an undifferentiated state when they go through at least 1 population doubling during a cultivation period of at least 3 weeks, while retaining at least about 50%, or the same proportion of cells bearing characteristic markers or morphological characteristics of undifferentiated cells after said cultivation period.

It is intended, for the purposes of the present invention, that the term pluripotent stem cell embraces any cell having the capacity for self-renewal and the potential to differentiate into one or more other cell types.

As used herein, the term "human pluripotent stem cell" (hPSC) refers to any human precursor cell that has the ability to form any adult cell.

"hPSC" as used herein, refer to precursor cells of human source that have the ability to form any adult cell. Such cells are true cell lines in that they: (i) are capable of extensive proliferation in vitro in an undifferentiated state; and (ii) are capable of differentiation to derivatives of all three embryonic germ layers (endoderm, mesoderm, and ectoderm) even after prolonged culture. Human embryonic stem cells (hESCs) are derived from fertilized embryos that are less than one week old (in the cleavage or blastocyte stage) or produced by artificial means (such as by nuclear transfer) that have equivalent characteristics. Other hPSC include, without being limited thereto, multipotent adult progenitor cells (MAPs), induced pluripotent stem cells (iPSC) and amniotic fluid stem cells.

hPSCs can be obtained using well-known cell-culture methods. For example, hESC can be isolated from single blastomeres of the cleavage or morula stage human embryo, from cleavage stage and morula human embryos and human blastocysts. Human embryos may be obtained from in vivo preimplantation embryos or more typically from in vitro fertilized (IVF) embryos. Alternatively, non-fertilized human oocyte can be parthenogenetically activated to cleave and develop to the blastocyst stage. In addition a single cell human embryo can be expanded to the blastocyst stage. For the isolation of hESCs from a blastocyst, the zona pellucida is removed and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by mechanical dissociation or by enzymatic digestion and the cells are then re-plated on a fresh tissue culture medium. Colonies demonstrating undifferentiated morphology are individually selected by micropipette, mechanically dissociated into clumps, and re-plated. Resulting ESCs are then routinely split every 1-2 weeks. For further details on methods of preparation of hESCs; see Thomson et al. [U.S. Pat. No. 5,843,780].

In the present invention, ES cells are not limited to a primary cell line collected from the inner cell mass, but may also be an established ES cell line. Examples of such an established ES cell line include: a cell line furnished from a cell population obtained by allowing the already established ES cell line to grow; and an ES cell line obtained by thawing a freeze-dried cell line and then culturing it. Such an established ES cell line is available without going through a step of disintegrating a fertilized egg.

Otherwise, the ES cells used in the present invention may be established from a single embryonic blastomere at the cleavage stage before the blastocyst stage, without impairing the generating ability of the embryo. Such ES cells can be obtained without destroying a fertilized egg.

Commercially available hPSCs can be also used in accordance with the invention. hPSCs can be purchased for example from the UK Stem Cell Banks or the NIH human embryonic stem cells registry. Non-limiting examples of commercially available embryonic stem cell lines are BG01, BG02, BG03, BG04, CY12, CY30, CY92, CY10, TE03, TE32, SA-01, VUB-01, H1, H9 and RC9.

More particularly, the present invention uses the human embryonic stem cell line RCe013-A (RC-9) derived as a failed to fertilise oocyte/1PN (pro-nuclear) embryo that was surplus to requirement or unsuitable for clinical use due to late development. Human embryonic stem cell (hESC) isolation, expansion and qualification was performed in a facilities whose specification, operation and monitoring complied with GMP standards enabling; i) a fully traceable procurement procedure with informed ethical consent which includes provision for commercial use, ii) detailed medical history and blood borne virus (BBV) screening of donors, and iii) compilation of a cell line history providing details on hESC manufacturing process and quality control testing regime.

For ethical reasons, the present invention preferably does not pertain to objects that may be considered as contrary to "ordre public" or morality. Therefore, in the context of the invention, the terms "human embryonic stem cells" preferably refer to human embryonic stem cells which isolation has not involved the destruction of an embryo. In other words, the terms "human embryonic stem cells" preferably exclude human embryonic stem cells isolated by techniques that involve the destruction of an embryo.

In the context of the invention, it is to be understood that any technique that does not involve the destruction of an embryo can be used, including those that are not described herein.

Moreover, in the context of the invention, the embryos used for obtaining human embryonic stem cells are preferably embryos that cannot give rise to a human being, such as embryos destined to be discarded following in vitro fertilization (IVF) and embryos created solely for the purpose of stem cell research.

Hence, in a yet preferred embodiment, the terms "human embryonic stem cells" (hESC) preferably refer to human embryonic stem cells isolated from discarded embryos, research embryos, or preferably isolated by techniques that do not involve the destruction of an embryo.

Alternatively, hES cells or human iPS cells may be selected from master cell banks that may be constituted in a therapeutic purpose. In a preferred manner, hES cells or human iPS may be selected to avoid or limit immune rejection in a large segment of the human population. Typically hES cells or human iPS cells are HLA-homozygous for genes encoding major histocompatibility antigens A, B and DR, meaning that they have a simple genetic profile in the HLA repertory. The cells could serve to create a stem cell bank as a renewable source of cells that may be suitable for preparing human skin substitutes for use in cell therapy of pathologies associated with skin damage (e.g. wound, burns, irradiation, disease-related abnormalities of epidermis . . . ). In another particular embodiment, human pluripotent stem cells may carry a mutation or a plurality of mutations that are causative for a genetic disease of the human skin.

The "induced pluripotent stem cell" in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, SalI4, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc.

Induced pluripotent stem cell was established by Yamanaka et al. in mouse cell in 2006. In 2007, Induced pluripotent stem cell was also established from human fibroblast, and has pluripotency and self-renewal competence similar to those of embryonic stem cells.

The terms "differentiation", "differentiating" or "derivatives thereof" as used herein denote a process by which an unspecialized or relatively less specialized cell becomes relatively more specialized. In the context of cell ontogeny, the adjective "differentiated" is a relative term. Hence, a "differentiated cell" is a cell that has progressed further down a certain developmental pathway than the cell it is being compared with. A relatively more specialized cell may differ from an unspecialized or relatively less specialized cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, etc., wherein such characteristics signify the progression of the differentiation towards the relatively more specialized cell.

In the present context, the method of the invention results in the progressive differentiation of human pluripotent stem cells and differentiating cells towards keratinocytes. Thus, as used herein, the term "differentiating" of differentiating cells to keratinocytes may be considered synonymous to the term "obtaining" keratinocytes from differentiating cells.

According to the present invention, the (human) pluripotent stem cells are grown without a feeder cell layer by culturing the cells on a protein matrix coating in the presence of a defined human stem cell medium.

Cultures of pluripotent stem cells are described as "undifferentiated" when a substantial proportion of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

More particularly, the present invention concerns an automated method for preparing keratinocytes derived from human pluripotent stem cells (hPSC) comprising or consisting in the steps of:

(a) forming and culturing aggregates or clumps of said pluripotent stem cells on a cell culture surface coated with a defined protein matrix solution to support cell attachment and growth in the presence of a defined human pluripotent stem cell medium;

(b) culturing the adherent aggregates or clumps of said pluripotent stem cells on a cell culture surface coated with a defined protein matrix coating in the presence of a defined keratinocyte culture medium comprising retinoïc acid and BMP4 to generate human keratinocyte progenitors;

(c) culturing the keratinocyte progenitors on a cell culture surface coated with a defined protein matrix coating in the presence of a defined keratinocyte culture medium devoid of retinoic acid and BMP4;

(d) treating the population of cells obtained in step c) to remove the non-conform cells and obtain an homogeneous population of keratinocytes, wherein at least one step of the automated method is performed by an apparatus for large-scale automated production of cells, without direct intervention from an operator.

In one embodiment of the invention, the pluripotent stem cells are either human induced pluripotent stem cells (hiPSC) or human embryonic stem cells (hESC).

In a preferred embodiment the human embryonic stem cell lines are chosen among BG01, BG02, BG03, BG04, CY12, CY30, CY92, CY10, TE03, TE32, SA-01, VUB-01, H1, H9 and RC9.

In a preferred embodiment the human induced pluripotent stem cell line is IPSC 1432.

According to the present invention, the population of interest or "conform" cells corresponds to cells that a small pavimentous shape.

According to the present invention, non-conform cells correspond to cells that have an elongated morphology or big shape.

According to the present invention, the term "homogeneous population of keratinocytes" corresponds to keratinocyte progenitors, and/or K5/K14 positive cells exhibiting a keratinocyte-like phenotype.

According to the present invention, the defined protein matrix solution used in culturing and maintaining human pluripotent stem cells is chosen in the group consisting of Matrigel™, L7 coating™, laminin, and vitronectin. Particularly, Matrigel™ or L7 coating™ is used to provide a substrate for cell culture and maintenance of human pluripotent stem cells.

According to the present invention, the human stem cell medium is a defined and serum-free medium. The defined serum-free medium refers to media with no unprocessed or unpurified serum or bovine pituitary extract (BPE) supplementation, and accordingly can include media with purified blood-derived components or animal tissue-derived components (such as growth factors). From the aspect of preventing contamination with heterogeneous animal-derived components, serum can be derived from the same animal as that of the stem cell(s).

The human stem cell medium according to the present invention may contain or may not contain any alternatives to serum. The alternatives to serum can include materials that appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. Alternatively, any commercially available materials can be used for more convenience. The commercially available materials include knockout Serum Replacement (KSR), Chemically-defined Lipid concentrated (Gibco), and Glutamax (Gibco).

The human stem cell medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

According to the present invention the human stem cell medium may be a commercial chemically defined medium. The human stem cell medium may be appropriately defined depending on the medium and stem cells used. The medium according to certain aspects of the present invention can be prepared using a medium used for culturing animal (human) cells as its basal medium, such as any of TeSR, Essential 8 medium Essential 8 CTS medium, StemFlex medium BME, BGJb, CMRL 1066, Glasgow MEM, Improved MEM Zinc Option, IMDM, Medium 199, Eagle MEM, aMEM, DMEM, Ham, RPMI 1640, StemPro, StemMACS iPS-Brew and Fischer's media, as well as any combinations thereof, but the medium is not particularly limited thereto as far as it can be used for culturing animal (human) cells.

For example, the following media are suitable to support hESC self-renewal:

a) StemPro® hESC SFM, containing DMEM/F-12 with GlutaMAX™ medium, Bovine serum albumin 1.8% (BSA), 10 ng/ml stabilized basic FGF and 2-Mercaptoethanol, b) CTS™ Essential 8™ Medium, containing 10 ng/ml stabilized basic FGF.

According to the present invention the human stem cell medium is a medium suitable to support hPSC self-renewal.

Generally, in manual culture methods, the day before the induction of the keratinocyte differentiation, the pluripotent stem cells are cut with a needle or another device and are further seeded in an appropriate culture medium.

According to the present invention, the day before the induction of the keratinocyte differentiation, the pluripotent stem cells are dissociated with EDTA and seeded at a cell density between 1000 and 10,000, preferably between 2000 and 8000, or preferably between 2000 and 4000, more preferably at 2000 or 4000 cells/cm².

According to the present invention, the day before the step b) of the automated method, the pluripotent stem cells are seeded at a cell density between 1000 and 10,000, preferably between 2000 and 8000, or preferably between 2000 and 4000, more preferably at 2000 or 4000 cells/cm².

According to the present invention, the cell dissociation reagent may be an enzymatic cell dissociation reagent, such as Trypsin, or Accutase, or a non-enzymatic cell dissociation reagent such as EDTA.

10 Applicants have discovered that variability in the generation and culture of differentiated cells can be reduced by choosing an optimal seeding density of the pluripotent stem cells.

In a preferred embodiment, hES RC9 are seeded at a cell density of 4000 cells/cm² under the form of clumps. In that case, the step c) of culturing the keratinocytes is ended after 18 days+/−2 days.

In another preferred embodiment, hiPS 1432 are seeded at a cell density of 2000 cells/cm² under the form of clumps. In that case, the step c) of culturing the keratinocytes is ended after 17 days +/−1 day.

According to the present invention, the pluripotent stem cells of a chosen cell line are counted and seeded repeatedly at the same cell density in order to standardize the time necessary to obtain keratinocyte progenitors and/or K5/K14 positive cells exhibiting a keratinocyte-like phenotype.

According to the present invention, the culturing in step (a) is not accomplished in the presence of a myosin light chain kinase inhibitor.

According to the present invention, the culturing in step (b) represents a step of induction (or initiation) of the keratinocyte differentiation which is initiated with two pulses of effective amounts of BMP-4 and retinoïc acid at Day 1 and Day 3 or Day 4, in the culture medium, in particular the defined keratinocyte Serum Free medium (dKSFM).

According to an embodiment of the invention, the concentration of retinoic acid in the keratinocyte culture medium may vary from 0.1 µM to 10 µM. In a particular embodiment the concentration of retinoic acid is 1 µM.

30 According to an embodiment of the invention, the concentration of BMP-4 in the keratinocyte culture medium may vary from 0.02 nM to 77 nM or 0.3 ng/ml to 1000 ng/ml. In a particular embodiment the concentration of BMP-4 is 0.273 nM.

An "effective amount" is an amount sufficient to effect beneficial or desired results. An effective amount can be administered in one or more administrations. An effective amount is an amount that is sufficient to promote differentiation of pluripotent stem cells into keratinocyte or expansion of keratinocyte progenitors.

According to the present invention, the culturing in step (b) or step (c) is not accomplished by contacting cells with an effective amount of any one or more of the factors, including, but not limited to ascorbic acid, cholera toxin, nicotinamide, a cyclic AMP analogue (e.g., 8-Br-CAMP), and a TGF RI Kinase Inhibitor II (TGFRKi).

According to the present invention, the culturing in step (b) is accomplished for a time period of 5 to 8 days, particularly 5, 6, 7 or 8 days, more particularly 6 days.

According to the present invention, human pluripotent stem cells (e.g. hES cells or human iPS cells) are cultivated for a time period sufficient for allowing the initiation of the differentiation of the human pluripotent stem cells into ketatinocytes in a medium in presence of retinoic acid and BMP4.

According to the present invention, human pluripotent stem cells (e.g. hES cells or human iPS cells) are cultivated for a time period sufficient for allowing the complete differentiation of said cells in a population of cells that recapitulate all morphological and functional attributes of human basal keratinocytes ("human keratinocytes derived from human pluripotent stem cells"). The complete differentiation of said cells into keratinocytes is accomplished in a medium without retinoic acid and BMP4.

According to a particular embodiment, the culturing in step (b) and in step (c) is preferably accomplished in the same defined keratinocyte Serum Free medium.

According to a particular embodiment, the time period for allowing the complete differentiation of said cells into keratinocytes is from 8 days to 25 days According to the present invention, the culturing in step (c) is accomplished for a time period of at least 8, 9, 10, 11, 12, 13, 14, 15, 16, 17, 18, 19, 20, 21, 22, 23, 24 or 25 days.

According to the present invention, the automated method for preparing keratinocytes derived from pluripotent stem cells comprises or consists in the steps of:

(a) forming and culturing aggregates or clumps of said pluripotent stem cells on a cell culture surface coated with a protein matrix to support cell attachment and growth in the presence of a defined human pluripotent stem cell medium;

(b) culturing the adherent aggregates or clumps of said pluripotent stem cells on a cell culture surface coated with a protein matrix in the presence of a defined keratinocyte culture medium comprising retinoic acid and BMP4 to generate keratinocyte progenitors for a time period of 5 to 8 days;

(c) culturing the keratinocyte progenitors on a cell culture surface coated with a defined protein matrix coating in the presence of a defined keratinocyte culture medium devoid of retinoic acid and BMP4 for a time period of 8 to 25 days;

(d) treating the population of cells obtained in step c) to remove the non-conform cells and obtain an homogeneous population of keratinocytes, wherein at least one step of the automated method is performed by an apparatus for large-scale automated production of cells, without direct intervention from an operator.

According to the present invention, the automated method for preparing keratinocytes derived from human embryonic stem cells comprises or consists in the steps of:

(a) forming and culturing aggregates or clumps of said embryonic stem cells on a cell culture surface coated with a protein matrix to support cell attachment and growth in the presence of a defined human pluripotent stem cell medium;

(b) culturing the adherent aggregates or clumps of said embryonic stem cells on a cell culture surface coated with a protein matrix at a cell density between 1000 and 10,000, preferably between 2000 and 8000, or preferably between 2000 and 4000, more preferably at 2000 or 4000 cells/cm² in the presence of a defined keratinocyte culture medium comprising retinoic acid and BMP4 to generate keratinocyte progenitors for a time period of 5 to 8 days;

(c) culturing the keratinocyte progenitors on a cell culture surface coated with a defined protein matrix coating in the presence of a defined keratinocyte culture medium devoid of retinoïc acid and BMP4 for a time period of 8 to 25 days, preferably 8 to 15 days, (d) treating the population of cells obtained in step c) to remove the non-conform cells and obtain an homogeneous population of keratinocytes, wherein at least one step of the automated method is performed by an apparatus for large-scale automated production of cells, without direct intervention from an operator.

According to the present invention, the automated method for preparing keratinocytes derived from human induced pluripotent stem cells comprises or consists in the steps of:

(a) forming and culturing aggregates or clumps of said induced pluripotent stem cells on a cell culture surface coated with a protein matrix to support cell attachment and growth in the presence of a defined human pluripotent stem cell medium;

(b) culturing the adherent aggregates or clumps of said induced pluripotent stem cells on a cell culture surface coated with a protein matrix at a cell density between 1000 and 10,000, preferably between 2000 and 8000, or preferably between 2000 and 4000, more preferably at 2000 or 4000 cells/cm² in the presence of a defined keratinocyte culture medium comprising retinoic acid and BMP4 to generate keratinocytes for a time period of 5 to 8 days;

(c) culturing the keratinocyte progenitors on a cell culture surface coated with a defined protein matrix coating in the presence of a defined keratinocyte culture medium devoid of retinoic acid and BMP4 for a time period of 8 to 25 days, preferably 8 to 13 days;

(d) treating the population of cells obtained in step c) to remove the non-conform cells and obtain an homogeneous population of keratinocytes, wherein at least one step of the automated method is performed by an apparatus for large-scale automated production of cells, without direct intervention from an operator.

According to a preferred embodiment, the step d) of the automated method is a two-step dissociation procedure comprising or consisting in washing and treating the cells enzymatically.

According to a preferred embodiment, the step d) of the automated method is a two-step dissociation procedure comprising or consisting in a first treatment with trypsin to remove the non-conform cells, and a second treatment with trypsin to detach the keratinocyte progenitors and/or the K5/K14 positive cells exhibiting a keratinocyte-like phenotype.

Preferably, cells are treated a first time with trypsin for a period of time sufficient to eliminate contaminant cells like fibroblasts or aged keratinocytes, and a second time with trypsin to detach the keratinocyte progenitors, and/or the K5/K14 positive cells exhibiting a keratinocyte-like phenotype.

Preferably, cells are first treated with trypsin for 2-3 minutes at 37° C. to eliminate contaminant cells like fibroblasts or aged keratinocytes. After removing trypsin, cells are secondary treated with trypsin during 5 to 10 minutes at 37° C. The harvested cells can either be banked or be amplified on defined matrix protein coated dishes (L7 matrix from Lonza or Collagen I from collagen Solution) with dKSFM or CnT-07.HC (CELLnTEC) medium until cell banking at the end of passage 1.

According to the present invention, the first enzymatic treatment with trypsin allows to remove more than 10% of cells, preferably between 10-20% of cells that are not keratinocyte progenitors, and/or K5/K14 positive cells exhibiting a keratinocyte-like phenotype.

In a preferred embodiment the enzymatic treatment is effected with trypsin, or trypsin-EDTA.

The enzymatic and non-enzymatic dissociation reagents are typically removed by centrifuging before the cells are transferred to fresh culture vessels.

In manual culture methods, enzymatic and non-enzymatic dissociation reagents are typically removed by centrifuging before the cells are transferred to fresh culture vessels. However, in the automated methods of the invention it is preferred that the passaging does not comprise a centrifugation step. This is, in part, due to the difficulty and considerable expense of integrating a centrifuge into an automated cell culture system. An advantage is to avoid exposing the cells to the shear forces that result from centrifugation.

It can also be noted that Accutase is not used in the present method. Indeed, the use of Accutase does not allow to selectively detach the non-conform cells from the appropriate coating substrate during the first enzymatic treatment. By using Accutase, a variable number of unwanted cells are still adherent to the collagen coating. The detachment of non-conform cells and also of keratinocytes occurs with Accutase after a longer duration of treatment than with trypsin.

According to the present invention, the automated method for preparing keratinocytes comprising more than 95, 96, 97, 98, 99% of K5+/K14+ keratinocytes further comprises (e) culturing the detached cells of step d) corresponding to the keratinocyte progenitors and/or the keratinocytes in the presence of a culture medium.

According to the present invention, the step e) of the automated method allows to prepare keratinocytes obtained after said culturing step comprising more than 95, 96, 97, 98, 99% of K5+/K14+ keratinocytes.

According to the present invention, step (e) is suitable to obtain a substantially pure homogenous population of human keratinocytes derived from human pluripotent stem cells.

According to a particular embodiment, the culturing in step (e) is preferably accomplished in the same keratinocyte Serum Free medium than in step (b) and in step (c).

The starting cells and the differentiated cells generally have differing requirements for culture medium and conditions. It is usual to carry out at least an initial stage of culture, after introduction of the differentiation factors, in the presence of medium and under culture conditions known to be suitable for growth of the starting cells. This is followed by a subsequent period of culture in the presence of a differentiation medium and under conditions known to be suitable for the differentiated cells. After a sufficient time for differentiation, the differentiated cells may be further cultured for expansion of the differentiated cells in an expansion medium.

According to one embodiment, the expansion phase is effected for at least 1 week, at least 2 weeks, at least 3 weeks, at least 4 weeks, at least 5 weeks, at least 6 weeks, at least 7 weeks, at least 8 weeks, at least 9 weeks or even 10 weeks. Preferably, the expansion phase is effected for 1 week-10 weeks, more preferably 2 weeks-10 weeks, more preferably, 3 weeks-10 weeks, more preferably 4 weeks-10 weeks, or 4 weeks-6 weeks.

According to the present invention, the remaining adherent cells are expanded over at least one passage.

According to a particular embodiment, the expansion phase is accomplished in the same keratinocyte Serum Free medium than in step (b), in step (c) and in step (e) on L7 matrix coated dishes or preferably with CnT07.HC on Collagen I coated dishes.

In a preferred embodiment, during the expansion phase, the medium is changed every 2-3 days.

According to still another embodiment, the keratinocytes and/or the differentiating cells that differentiate toward keratinocytes are passaged at least 1 time during the expansion phase, at least twice during the expansion phase, at least three times during the expansion phase, at least four times during the expansion phase, at least five times during the expansion phase, or at least six times during the expansion phase.

Harvesting of the expanded population of keratinocytes and/or the differentiating cells may be effected using methods known in the art (e.g. using an enzyme such as trypsin).

In one embodiment, the passaging includes counting the cells transferred from the first culture vessel. Following counting, the predetermined number of cells is transferred to each of the further culture vessels.

A culture vessel used for culturing the cell(s) of the present invention can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, as long as it is capable of culturing the cells therein. The stem cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture.

The automated process of the method is presented in FIG. 2.

In one embodiment passaging requires dissociation of the differentiating cells, the dissociation is conveniently carried out by adding a cell dissociation reagent to the first culture vessel. The cell dissociation reagent may be an enzymatic cell dissociation reagent, such as trypsin-EDTA.

In one embodiment, the passaging includes counting the cells transferred from the culture vessel containing the differentiated cells obtained after step d), preferably using an automated cell counting device forming part of the robotic cell culture apparatus. Following counting, the predetermined number of cells is transferred to each of the further culture vessels.

In other embodiment, the actual number of cells transferred from the first culture vessel is not counted. Rather, the number of cells is estimated based on the size of the culture vessel and the growth characteristics of the Keratinocytes and/or the differentiating cells under the particular culture regime being used. Thus, the passaging can comprise calculating the number of cells transferred from the first culture vessel based on one or more of (i) the initial number of Keratinocytes and/or the differentiating cells in the first culture vessel, (ii) the population doubling time of the Keratinocytes and/or the differentiating cells, (iii) the culture area of the first culture vessel, and (iv) the culture volume. It will be appreciated that the culture area of the first culture vessel is particularly relevant when calculating the number of adherent keratinocytes and/or the differentiating cells obtained after a given period of culture, whereas the culture volume will be particularly relevant when calculating the number of keratinocytes in suspension.

Alternatively, it is an option to passage the cells so that the cells from the first culture vessel are divided between a predetermined number of further culture vessels. For example, in preferred embodiments of the invention, Keratinocytes and/or the differentiating cells that differentiate toward Keratinocytes and/or the differentiating cells are passaged with a split ratio of from 1:2 to 1:10, preferably from 1:2 to 1:5.

In further embodiments of the invention, passaging is carried out when the Keratinocytes and/or the differentiating cells that differentiate toward keratinocytes in the first culture vessel reach a predetermined percentage confluence. Typically, the passaging is carried out when the Keratinocytes and/or the differentiating cells that differentiate toward Keratinocytes in the first culture vessel are 50 to 100% confluent, preferably 60 to 90% confluent, more preferably 70 to 80% confluent.

In further embodiments of the invention, passaging is carried out with a cell seeding density between 10,000 and 100,000, preferably between 20,000 and 50,000, more preferably between 30,000 and 40,000 cells/cm$^2$.

In the automated method of the invention, it is desirable, that the percentage confluence is calculated rather than being determined prior to each passage by the operator. Thus, in preferred embodiments, the percentage confluence is calculated based on one or more of (i) the number of the keratinocytes that differentiate toward keratinocytes initially present in the culture vessel, (ii) the population doubling time of the keratinocytes and/or the differentiating cells that differentiate toward keratinocytes, (iii) the culture area of the first culture vessel. In other embodiments, confluence is recorded and/or estimated automatically.

In a preferred embodiment, the passages comprises (i) dissociating the differentiated cells or keratinocytes in a first vessel to obtain a cell suspension; (ii) transferring the dissociated keratinocytes to new culture vessels at a cell seeding density between 10,000 and 100,000, preferably between 20,000 and 50,000, more preferably between 30,000 and 40,000 cells/cm$^2$; and (iii) culturing the keratinocytes until the keratinocytes are 50 to 100% confluent, wherein the passages does not comprise a centrifugation step.

Preferably the passaging is repeated until either a predetermined number of culture vessels containing the Keratinocytes and/or the differentiating cells that differentiate toward Keratinocytes or a predetermined number of the Keratinocytes and/or the differentiating cells that differentiate toward Keratinocytes has been produced. In some embodiments, the point at which the predetermined number of Keratinocytes has been produced will be estimated based on the growth characteristics of the Keratinocytes and/or the differentiating cells that differentiate toward Keratinocytes and the previous process steps (e.g. the number of passages). It is also possible to calculate the number of the differentiating cells or Keratinocytes obtained by calculating the yield per culture vessel and multiplying this value by the number of culture vessels containing the Keratinocytes and/or the differentiating cells that differentiate toward Keratinocytes that have been produced.

According to a further embodiment of the invention, the medium in which the hPSCs are differentiated is any known cell culture medium known in the art for supporting cell growth in vitro, typically, a medium comprising a defined base solution, which includes salts, sugars, amino acids and any other nutrients required for the maintenance of the cells in the culture in a viable state.

According to some embodiments of the present application, steps (a), (b), (c) and (e) of the automated method include replacing periodically all or a portion of the culture medium. For example, all or a proportion of the culture medium can be removed from the culture vessel by pipetting or by pouring used medium to waste and fresh medium can then be added. If medium is to be removed by pipetting, the culture vessel can be positioned to assist removal of the medium.

The proportion of medium volume replaced or added will vary between different embodiments of the invention and may be 10%, 20%, 30%, 40%, 50%, 60%, 70%, 80%,90% or 100% of the culture volume or surface.

The automated method of the invention can be adapted for use with any type of culture vessel, including tissue culture flasks, dishes and multi-well plates. However, it is convenient to use flasks when producing large numbers of Keratinocytes, as this advantageously reduces the number of processing steps required to obtain a given number of cells and thus reduces the potential for cell damage during handling.

In one embodiment, T75 or T175 tissue culture vessels are used.

In another embodiment, culture chambers (e.g. Cell-Stack®) are used.

According to one embodiment, the cells in steps a) to e) are cultured on adherent substrate under normal atmospheric oxygen conditions.

Examples of adherent substrates include but are not limited to fibronectin, laminin, polyD-lysine, collagen and gelatin.

According to a preferred embodiment of the invention, the proliferation/growth medium is free of xeno contaminants i.e. free of animal derived components such as serum, animal derived growth factors and albumin.

Following harvesting, the expanded population of the Keratinocytes and/or the differentiating cells may optionally be cryopreserved using methods known in the art. Examples of media suitable for cryopreservation include but are not limited to 90% Human Serum/10% DMSO, CryoStor 10%, 5% and 2%, and Stem Cell Banker.

Characterization of the Cells

In one embodiment, the differentiation of human pluripotent stem cells toward keratinocytes is monitored throughout the process using an automated live-cell imaging system that resides within the controlled environment of the automated cell culture platform. This non-invasive cell imaging system provides cell confluence metrics in real-time as well as phase contrast images of processed culture vessels. Each step of the differentiation protocol is thus monitored to prevent deviations from specification limits.

Description of the Apparatus

The apparatus used to implement the automated method of the present invention is selected from any of a number of automated platforms for cell culture that are available and adapted for large-scale production of stem cells or differentiated cells derived from stem cells.

The Applicant has obtained good results using the CompacT SelecT® platform, manufactured by Sartorius, but it will be understood that other systems can be adapted to provide apparatus according to the invention, which can be used to carry out the methods of the invention.

In one embodiment, the invention provides apparatus adapted or arranged for carrying out the methods of the invention. Thus, the invention provides an apparatus for large-scale automated production of cells comprising: a) robotic means for handling culture vessels; b) means for inoculating cells into a culture; c) means for changing or adding medium to a culture; and d) programmable control means; wherein the apparatus is adapted to the differentiation of hPSCs toward Keratinocytes and their amplification.

Such means are conveniently provided using an automated pipetting station, preferably using disposable pipettes, and, optionally, additional liquid pumps, thus permitting programmable medium selection and additive dispensing of different media and or reagents without risk of cross-contamination.

Thus, the apparatus may further comprise means for adding further components to a culture. In some embodiments, separate systems will be provided for adding or removing media, reagents and/or cells to and from culture vessels of different types. For example, the apparatus may comprise separate dispensing stations for tissue culture flasks and multi-well plates. Additional means may also be supplied, e.g. for adding growth factors or cell dissociation reagents.

The apparatus also includes incubators for any culture vessel format described herein, typically including at least one of an incubator for flasks and an incubator for tissue culture plates. In use, the apparatus will typically provide control of one or more of the temperature, the $CO_2$ level, the $O_2$ level and the relative humidity at which the stem cells are cultured.

The apparatus will also provide aseptic conditions to prevent contamination of cultures and ensure operator safety, suitably using a negative pressure laminar airflow hood.

In preferred embodiments the apparatus also comprises means for automated cell counting to provide consistent and accurate cell densities when seeding new culture vessels. Means for automated determination and/or estimation of percentage confluence can also be included.

The apparatus can also comprise imaging equipment or other detection means. Such means can, for example, be used to detect the expression of fluorescent reporter genes (e.g. GFP) in the cells being cultured. For example, the cells may express a reporter gene, optionally provided by means of a construct comprising an internal ribosome entry site (IRES). The percentage of reporter-positive cells can be used to determine when to passage or induce differentiation of the stem cells in a culture. Imaging equipment can also be used to assess when to harvest cells.

According to the invention, the apparatus incorporates a small six-axis anthropomorphic robotic arm that can access 90 T175 culture vessels and 210 plate incubators. The system allows the automation of seeding, feeding and other cell culture processes in order to maintain cell lines in standard cell culture vessels. Culture vessels are bar-coded for identification and cell process tracking. Two culture vessels decappers and flask holders, automated medium pumping and an automatic cell counter are integrated within a high-efficiency particulate air (HEPA) filtered cabinet to ensure sterility.

In one embodiment, the CompacT SelecT® has also been shown to be successful at preventing contamination when the GMP version of the CompacT SelecT® passed the sterile fill tests.

In one embodiment, the CompacT SelecT® allows activities during cell culture such as seeding, media changes and measurement cells in a controlled environment. Thus this platform can be used to expand and differentiate batches of cells to a tighter specification than manual cell culture.

The automation enables scale out for conventional formats with predictable process variation and quality outcome by removing manual interventions. The CompacT SelecT® is a preferred platform for the development of processes permiting the automated cell culture of adherent cells.

The Cells Obtained by the Method and their Uses

The human keratinocytes derived from human pluripotent stem cells obtainable by the method as above described are able to recapitulate morphological attributes of human basal keratinocytes as well as expressing markers of basal keratinocytes that include markers of basal layer with keratin 5 and 14 (K5/K14).

According to the present invention, the keratinocyte express cytokeratin 5 and cytokeratin 14.

The keratinocytes of the present invention can be characterized according to a number of phenotypic criteria. The criteria include but are not limited to the detection or quantification of expressed cell markers, enzymatic activity, and the characterization of morphological features and intercellular signaling.

The keratinocytes of the present invention have morphological features characteristic of keratinocyte stem cells in nature. One or more such features present in a single cell are consistent with the cell being a member of the keratinocyte stem cell lineage. Cells of this invention can also be characterized according to whether they express phenotypic markers characteristic of the keratinocyte lineage. General epidermal keratinocytes are characterized as expressing cytokeratin 5, and cytokeratin 14. Within such a population, there are colony forming keratinocyte stem cells and keratinocyte progenitors on route to terminal differentiation.

The substantially pure homogenous population of human keratinocytes derived from human pluripotent stem cells of the invention may be also suitable for preparing human epidermis.

In a particular embodiment, human epidermis substitutes according to the invention may be generated as described by Poumay, Y et al. 2004. Culture of the substantially pure homogenous population of human keratinocytes derived from human pluripotent stem cells of the invention may be performed on polycarbonate culture inserts. These cells may be maintained for 5 to 7 days in CnT07.HC medium (amplification phase) and 14 days in 3D Prime CnT medium (CELLnTEC) for stratification. The cells may be exposed to the air-liquid interface by removing the culture medium in the insert for 14 days for stratification. Organotypic cultures may then grown submerged up to keratinocyte confluence, and finally maintained at the air-liquid interface for 14 days to enhance stratification and differentiation of the epithelium. For in vivo testings, human epidermis substitutes according to the invention may be generated with the substantially pure homogenous population of human keratinocytes derived from human pluripotent stem cells seeded on a plasma based matrix (fibrin) for 7 to 10 days in CnT07.HC medium to obtain a monolayer of keratinocytes.

A further object of the invention relates to a human epidermis substitutes obtainable by the method as above described.

A further object of the invention relates to a method for grafting an animal (in vivo testings), preferably a mammal, more preferably a mouse, with a human skin substitute as described above. In a particular embodiment said animal is an immunodeficient animal (e.g. NOD/SCID or Nude mouse). Said method may be useful to provide animal models for human skin.

In a particular embodiment, animals grafted with a human skin substitute of the invention may be generated as described by Del Rio M. et al. (2002). Briefly, animals are shaved and aseptically cleansed. Full-thickness wounds are then created on the dorsum of mice and finally grafting with the human skin substitute of the invention is performed under sterile conditions. 10-12 weeks may be then sufficient to obtain a human skin on said animal.

In a particular embodiment, animals grafted with a human skin substitute of the invention may be generated by "in house" method. Briefly, animals are shaved and aseptically cleansed. Full-thickness wounds are then created on the dorsum of mice and finally applied with the human skin substitute of the invention is performed under sterile conditions. Faty gauzes are put on the graft area. The graft and the fatty gauzes are put inside the mouse skin borders to avoid suturing. The piece of mouse skin is devitalized by manual liquid nitrogen and PBS1X bath cycles and resutured on the graft to provide the graft with a "biological" dressing. 10-12 weeks may be then sufficient to obtain a human skin on said animal.

A further object of the invention relates to an animal model for human skin obtainable according to the automated method as above described.

The human skin substitutes and animal models of the present invention may have a variety of uses. These uses include, but are not limited to, use for screening compounds, substrates for culturing tumors and pathological agents (e.g., human papilloma virus), and for modelling human injuries or pathologies associated with skin damage.

For example human skin substitutes and animal models of the present invention may be used for a variety of in vitro and in vivo tests. In particular but in non limiting way, the human skin substitutes and animal models of the present invention find use in the evaluation of: skin care products, drug metabolism, cellular responses to test compounds, wound healing, phototoxicity, dermal irritation, dermal inflammation, skin corrosivity, and cell damage. Typically, for animal models of the invention, the product may be administered topically on the human skin, or may be administered through an oral, sublingual, subcutaneous, intramuscular, intravenous, and transdermal route.

The present invention encompasses a variety of screening assays. In some embodiments, the screening method comprises providing a human skin substitute or an animal model of the present invention and at least one test compound or product (e.g., a skin care product such as a moisturizer, cosmetic, dye, or fragrance; the products can be in any from, including, but not limited to, creams, lotions, liquids and sprays), applying the product or test compound to said human skin substitute or animal model, and assaying the effect of the product or test compound on the human skin substitute or animal model. Typically, for animal models of the invention, the test compound or product may be administered topically on the human skin, or may be administered through an oral, sublingual, subcutaneous, intramuscular, intravenous, and transdermal route. A wide variety of assays may be used to determine the effect of the product or test compound on the human skin substitute or animal model. The assays may be directed to the toxicity, potency, or efficacy of the compound or product. Additionally, the effect of the compound or product on growth, barrier function, or tissue strength can be tested.

In other preferred embodiments, the human skin substitutes or animal models of the invention find use for screening the efficacy of drug introduction across the skin. In a particular embodiment, the human skin substitutes or animal models of the present invention are also useful for the culture and study of tumours that occur naturally in the skin as well as for the culture and study of pathogens that affect the skin. Accordingly, in some embodiments, it is contemplated that the human skin substitutes or animal models of the present invention are seeded with malignant cells. These reconstructed human skin substitutes or animal models can then be used to screen compounds or other treatment strategies (e.g., radiation or tomotherapy) for efficacy against the tumour in its natural environment. In some embodiments of the present invention provide methods comprising providing a reconstructed human skin substitute or animal model infected with a pathogen of interest and at least one test compound or treatment and treating the skin substitute or animal model with the test compound or treatment.

In another particular embodiment, the human skin substitutes or animal models of the present invention are also useful for modelling human injuries or pathologies associated with skin damage. For example, the human skin substitutes and animal models of the present invention may provide both in vitro and in vivo models for modelling wounds, burns (e.g. fire burns, sunburns . . . ), or lesions caused by irradiations, pathogens . . . , irritations caused by chemical products or environment conditions, degenerative diseases and genetic diseases. In certain embodiments, pathologies of interest are genodermatosis such as Epidermolysis bullosa, Xeroderma pigmentosum, ichthyosis, ecto-dermal dysplasia, kindler syndrome, Sickle cell leg ulcer and others.

Typically, the human skin substitutes or animal models of the present invention may be generated form pluripotent stem cells that may carry a mutation or a plurality of mutations that are causative for a genetic disease of the human skin. Both in vitro and in vivo models as described above may have particular interests for medical research or may be useful for screening compounds for the treatment or the prevention of said injuries and pathologies.

In particular, the present invention contemplates the use of the human skin substitutes and animal models according to the invention for screening of compounds from libraries, in particular combinatorial libraries, using e.g. high throughput or high content techniques. Typically, for animal models of the invention, the test compound or product may be administered topically on the human skin, or may be administered through an oral, sublingual, subcutaneous, intramuscular, intravenous, and transdermal route.

In a further aspect of the invention, the human skin substitutes of the present invention may be used for the treatment of a pathology associated with skin damage. Therefore the present invention relates to a method for the treatment of a pathology associated skin damage comprising a step consisting of grafting a patient in need thereof with a human skin substitute of the invention. For example, the human skin substitutes of the present invention find use in wound closure and burn treatment applications. The use of grafts for the treatment of burns and wound closure is described, for example in U.S. Pat. Nos. 5,693,332. Accordingly, the present invention provides methods for wound closure, including wounds caused by burns, comprising providing a human skin substitute according to the present invention and a patient suffering from a wound and grafting the patient with the human skin substitute under conditions such that the wound is closed.

The substantially pure homogenous population of human keratinocytes derived from human pluripotent stem cells obtained according to the method of the invention is then suitable for skin therapy.

Therefore the invention relates to a pharmaceutical composition comprising a substantially pure homogenous popu-lation of human keratinocytes derived from human pluripotent stem cells of the invention and optionally a pharmaceutically acceptable carrier or excipient. In certain embodiments, a pharmaceutical composition may further comprise at least one biologically active substance or bio-active factor.

As used herein the term "biologically active substance or bioactive factor" refers to any molecule or compound whose presence in a pharmaceutical composition of the invention is beneficial to the subject receiving the composition. As will be acknowledged by one skilled in the art, biologically active substances or bioactive factors suitable for use in the practice of the present invention may be found in a wide variety of families of bioactive molecules and compounds. For example, a biologically active substance or bioactive factor useful in the context of the present invention may be selected from anti-inflammatory agents, anti-apoptotic agents, immunosuppressive or immunomodulatory agents, antioxidants, growth factors, and drugs.

A related aspect of the invention relates to a method for treating a subject suffering from a pathology associated with skin damage, said method comprising a step of administering to the subject an efficient amount of a substantially pure homogenous population of human keratinocytes derived from human pluripotent stem cells of the invention (or a pharmaceutical composition thereof).

As used herein, the term "efficient amount" refers to any amount of a substantially pure homogenous population of human keratinocytes derived from human pluripotent stem cells (or a pharmaceutical composition thereof) that is sufficient to achieve the intended purpose.

The substantially pure homogenous population of human keratinocytes derived from human pluripotent stem cells (or a pharmaceutical composition thereof) of the invention may be administered to a subject using any suitable method. The substantially pure homogenous population of human kera-tinocytes derived from human pluripotent stem cells of the invention may be implanted alone or in combination with other cells, and/or in combination with other biologically active factors or reagents, and/or drugs. As will be appreciated by those skilled in the art, these other cells, biologi-cally active factors, reagents, and drugs may be administered simultaneously or sequentially with the cells of the invention.

In certain embodiments, a treatment according to the present invention further comprises pharmacologically immunosuppressing the subject prior to initiating the cell-based treatment. Methods for the systemic or local immu-nosuppression of a subject are well known in the art. Effective dosages and administration regimens can be readily determined by good medical practice based on the nature of the pathology of the subject, and will depend on a number of factors including, but not limited to, the extent of the symptoms of the pathology and extent of damage or degeneration of the tissue or organ of interest, and characteristics of the subject (e.g., age, body weight, gender, general health, and the like).

The invention will be further illustrated by the following figures and examples.

EXAMPLES

Figure 1:
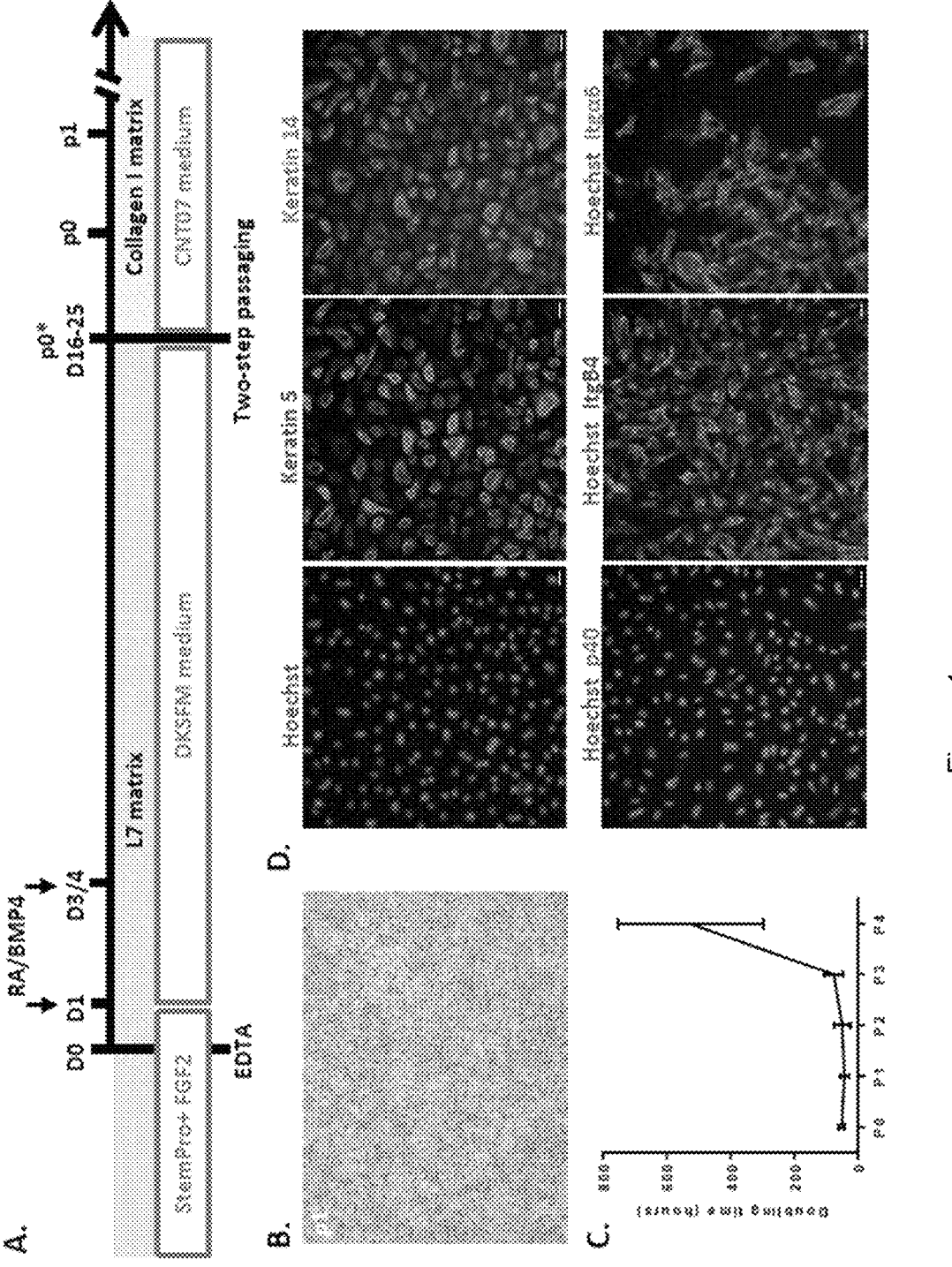
FIG. 1: Automated differentiation and amplification of a pure population of hPSC-derived keratinocytes. (A) Schematic representation of the differentiation strategy to generate keratinocytes from hPSCs. (B) Representative macroscopic observation of the hESC RC9 line after keratinocyte derivation and amplification (KER-RC9). (C) Doubling time of KER-RC9 during sequential passages. (D) Representative immunofluorescence analysis for keratinocyte markers keratin 5, keratin 14, p40, Itgβ4 and Itgα6 of KER-RC9 at P1. Scale: 10 μm.
Figure 2:
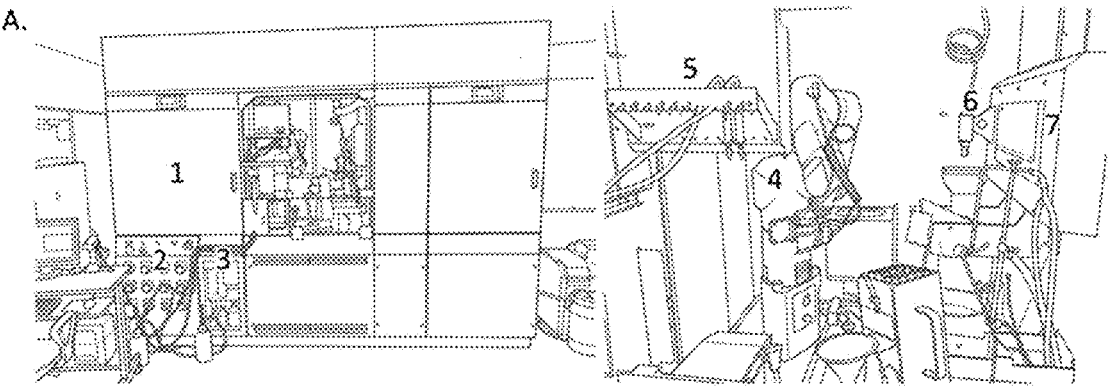
FIG. 2: Automated process to differentiate hPSCs into keratinocytes using the CompacT SelecT system. (A) Overview of the automated CompacT SelecT cell culture system: (1) T-flask carousel incubator, (2) Media peristaltic pumps, (3) Cedex automated cell counter, (4) 6-axis robotic arm, (5) Flask decappers, (6) Pipette head and (7) IncuCyte live cell analysis system. (B) Automated process to generate large banks of keratinocytes from hPSCs.
Figure 2:
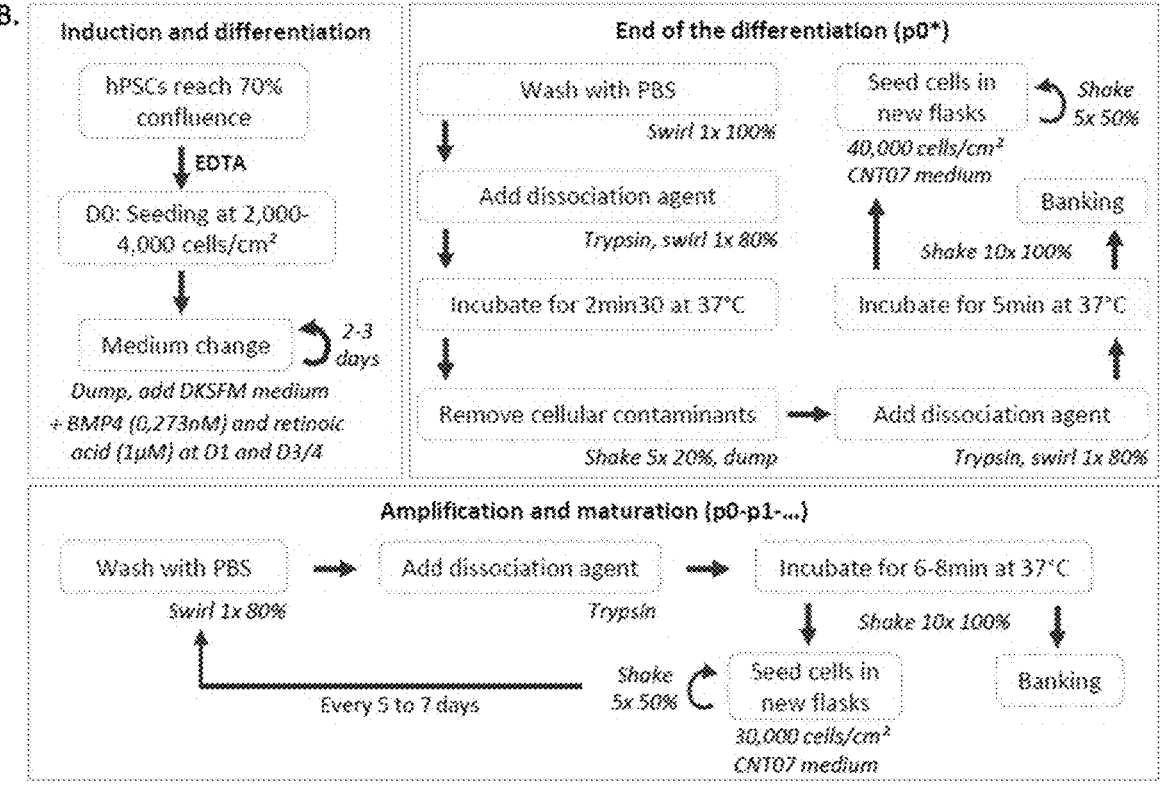

1. Preparation of Keratinocytes from hiPSC
Manual hiPSC Culture

Human iPSC 1432 line was used and cultured in feeder free conditions using iPS Brew™ medium (Miltenyi) and vitronectin coating (Life Technologies). Cells were plated and grown until they reached 80 percent of confluence.
Differentiation of hiPSC Cells in Keratinocytes hiPSC 1432 cells were incubated with EDTA at 37° to obtain clumps that were then seeded in a defined human stem cell medium for 1 day and then in the defined Keratinocyte SFM (dKSFM-Gibco—Thermo Fisher Scientific) which is a serum-free medium optimized for the isolation and expansion of human keratinocytes without the need for bovine pituitary extract (BPE) supplementation or the use of fibroblast feeder layers. The induction of ectodermal differentiation was done when 0.273 nM of human recombinant BMP-4 (Peprotech) and 1 μM of trans retinoic acid (Sigma) were added on day 1 and day 3 or 4. Cells were grown in the same medium until clones of epithelial cells were isolated.

During all the differentiation process the medium was changed every 2/3 days.

At the end of differentiation, cells are isolated and purified with differential trypsinization. Briefly, cells are first treated with trypsin for 2-3 minutes in 37° C. to eliminated contaminant cells like fibroblasts. After discarding trypsin, cells are secondary treated with trypsin during 5 to 10 minutes at 37° C. The harvested cells are either banked or amplified on collagen I coated dishes with CnT-07.HC medium
Macroscopic Analysis of hiPSC 1432 Line During the Differentiation Process The morphology of the cells is monitored throughout the differentiation process and during the amplification phase. From day 3, cells present a differentiated cell morphology with large cells organized in colonies distinct from that of pluripotent stem cells. At day 8, the differentiating colonies are still growing and present 2 distinct morphologies: the centre part is composed of small cells and the outer part (like a ring around the centre part) is composed of migrating bigger cells (not shown).

The methods according to the present invention allow the preparation of iPSC-derived keratinocytes that provide an homogeneous and pure population of keratinocytes.
2. Preparation of Keratinocytes from hESC
Manual hESC Culture Human embryonic stem cell RC-9 line was used and cultured in feeder free conditions using StemPro medium (Gibco—Thermo Fisher Scientific) supplemented with stabilized FGF-2 on L7 matrix (Lonza). Cells were plated and grown until they reached 80 percent of confluence.

Differentiation of hPSC Cells in Keratinocytes hES RC9 cells were incubated with EDTA at 37° to obtain clumps that were then seeded in a defined human stem cell medium for 1 day and then in the defined Keratinocyte SFM (dKSFM-Gibco—Thermo Fisher Scientific) which is a serum-free medium optimized for the isolation and expansion of human keratinocytes without the need for bovine pituitary extract (BPE) supplementation or the use of fibroblast feeder layers. The induction of ectodermal differentiation was done when 0.273 nM of human recombinant BMP-4 (Peprotech) and 1 μM of trans retinoic acid (Sigma) were added on day 1 and day 3 or 4. Cells were grown in the same medium until clones of epithelial cells were isolated. During all the differentiation process the medium was changed every ⅔ days. The morphology of the cells is monitored throughout the differentiation process and during the amplification phase. From day 3, cells present a differentiated cell morphology with large cells organized in colonies distinct from that of pluripotent stem cells. At day 8, the differentiating colonies are still growing and present 2 distinct morphologies: the centre part is composed of small cells and the outer part (like a ring around the centre part) is composed of migrating bigger cells.

At the end of differentiation, cells are isolated and purified with differential trypsinization. Briefly, cells are first treated with trypsin for 2-3 minutes in 37° C. to eliminate contaminant cells. After discarding trypsin, cells are secondary treated with trypsin during 5 to 10 minutes at 37° C. The harvested cells are either banked or amplified on collagen I coated dishes with CnT-07.HC medium.
Immunostaining Cells were fixed in 4% PFA for 10 min at room temperature (RT) and rinsed 3 times with PBS. After 1 hour in blocking solution (PBS containing 1% BSA) at RT, cells were incubated overnight à 4° C. with primary antibodies at appropriate dilutions. After 3 washes in PBS, Alexa Fluor-conjugated secondary antibodies (Invitrogen) were added at 1:1000 for 45 min at RT.

Representative immunofluorescence analysis for keratinocyte markers keratin 5, keratin 14, p40, Itgβ4 and Itgα6 of KER-RC9 are shown at passage 1 (see FIG. 1D).

As shown in FIG. 1, the methods according to the present invention allow the preparation of hPSC-derived keratinocytes that provide an homogeneous and pure population of keratinocytes.

The invention claimed is:
1. An automated method for preparing keratinocytes derived from human pluripotent stem cells (hPSC), the method comprising:
(a) forming and culturing aggregates or clumps of said pluripotent stem cells on a cell culture surface coated with a protein matrix that supports cell attachment and growth, in the presence of a defined human pluripotent stem cell medium;
(b) culturing the adherent aggregates or clumps of said pluripotent stem cells on a cell culture surface coated with a protein matrix in the presence of a defined keratinocyte culture medium comprising retinoic acid and BMP4 so as to generate keratinocyte progenitors;
(c) culturing the keratinocyte progenitors on a cell culture surface coated with a defined protein matrix coating in the presence of a defined keratinocyte culture medium devoid of retinoic acid and BMP4;
(d) treating a population of the cells obtained in the culturing c) so as to remove non-conform cells and obtain a homogeneous population of keratinocytes, wherein the cells are treated a first time with trypsin-EDTA during a time in a range from 2 to 3 minutes at 37° C. so as to eliminate contaminant cells, the contaminant cells comprising fibroblasts and aged keratinocytes, and a second time with trypsin-EDTA a time in a range from 5 to 10 minutes at 37° C. so as to detach the keratinocyte progenitors, or K5/K14 positive cells exhibiting a keratinocyte-like phenotype, or a combination thereof; and (e) culturing the detached cells resulting in the treating d) corresponding to the keratinocyte progenitors, or the keratinocytes, or a combination thereof, in the presence of a culture medium, wherein the keratinocytes obtained after the culturing (e) comprise more than 99% of K5+/K14+ keratinocytes, and wherein at least one process selected from the (a)-(e) in the automated method is performed by an apparatus for large-scale automated production of cells, without direct intervention from an operator.

2. The automated method for preparing keratinocytes according to claim 1, wherein a day before of the culturing b), the pluripotent stem cells are seeded at a cell density in a range from 1000 to 10,000 cells/cm$^2$.

3. The automated method for preparing keratinocytes according to claim 1, wherein the human pluripotent stem cell medium is a medium that supports hPSC self-renewal.

4. The automated method for preparing keratinocytes according to claim 1, wherein the culturing (b) is performed for a time period in a range from 5 to 8 days.

5. The automated method for preparing keratinocytes according to claim 1, wherein the culturing (c) is performed for a time period of at least 8, 9, 10, 11, 12, 13, 14, 15, 16, 17, 18, 19, 20, 21, 22, 23, 24 or 25 days.

6. The automated method for preparing keratinocytes according to claim 1, the method comprising:

(a) the forming and culturing aggregates or clumps of said pluripotent stem cells on a cell culture surface coated with a protein matrix that supports cell attachment and growth in the presence of a defined human pluripotent stem cell medium;

(b) the culturing the adherent aggregates or clumps of said pluripotent stem cells on a cell culture surface coated with a protein matrix in the presence of a defined keratinocyte culture medium comprising retinoic acid and BMP4 so as to generate keratinocyte progenitors for a time period in a range from 5 to 8 days;

(c) the culturing the keratinocyte progenitors on a cell culture surface coated with a defined protein matrix coating in the presence of a defined keratinocyte culture medium devoid of retinoic acid and BMP4 for a time period in a range from 8 to 25 days; and (d) the treating the population of cells obtained in the culturing c) so as to remove the non-conform cells and obtain a homogeneous population of keratinocytes.

7. The automated method according to claim 1, wherein remaining adherent cells are configured to be banked or expanded over at least one passage.

8. The automated method according to claim 7, wherein the at least one passage comprises:

(i) dissociating differentiated cells or keratinocytes in a first vessel so as to obtain a cell suspension;

(ii) transferring the dissociated keratinocytes to new culture vessels at a cell seeding density in a range from 10,000 to 100,000 cells/cm$^2$; and (iii) culturing the keratinocytes until the keratinocytes are from 50 to 100% confluent, wherein the at least one passage does not comprise centrifugation.

9. The automated method according to claim 1, wherein the method is carried out with an apparatus for large-scale automated production of cells, the apparatus comprising:

a) a robotic vessel handler that handles culture vessels;

b) a cell seeder that inoculates cells into a culture;

c) a medium exchanger that changes or adds medium to a culture; and d) a programmable control;

wherein the apparatus is adapted to the differentiation of hPSCs toward keratinocytes and their amplification.

10. The automated method for preparing keratinocytes according to claim 1, wherein the keratinocyte expresses cytokeratin 5 and cytokeratin 14.

11. The automated method for preparing keratinocytes according to claim 2, wherein the cell density is in a range from 2000 and 8000 cells/cm$^2$.

12. The automated method for preparing keratinocytes according to claim 2, wherein the cell density is in a range from 2000 and 4000 cells/cm$^2$.

* * * * *